(12) United States Patent
Estanove et al.

(10) Patent No.: US 6,855,697 B1
(45) Date of Patent: Feb. 15, 2005

(54) TROXERUTIN WITH A HIGH CONTENT OF TRIHYDROXYETHYLRUTOSIDE AND PROCESS FOR ITS PREPARATION

(75) Inventors: Cyril Estanove, Boulogne (FR); François Pruvost, Quimper (FR)

(73) Assignee: Negma-Lerads, Toussus-le-Noble (FR)

( * ) Notice: Subject to any disclaimer, the term of this patent is extended or adjusted under 35 U.S.C. 154(b) by 0 days.

(21) Appl. No.: 09/857,846

(22) PCT Filed: Dec. 10, 1999

(86) PCT No.: PCT/FR99/03100

§ 371 (c)(1),
(2), (4) Date: Jun. 11, 2001

(87) PCT Pub. No.: WO00/35933

PCT Pub. Date: Jun. 22, 2000

(30) Foreign Application Priority Data

Dec. 11, 1998 (FR) ............................................. 98 15710

(51) Int. Cl.[7] ................ A61K 31/7028; A61K 31/7042; C07H 17/07
(52) U.S. Cl. ............................. 514/27; 514/27; 514/25; 536/4.1
(58) Field of Search ..................................... 514/27, 25

(56) References Cited

U.S. PATENT DOCUMENTS 3,420,815 A * 1/1969 Courbat .......................... 536/8

FOREIGN PATENT DOCUMENTS

FR    2 267 327 A    11/1975
GB    1 497 157        1/1978

OTHER PUBLICATIONS

H. Cai et al., "Purification of (hydroxyethyl)rutin Derivatives", Chemical Abstracts, vol. 113, No. 17, pp. 832 (Oct. 22, 1990).

* cited by examiner

Primary Examiner—Samuel Barts
Assistant Examiner—Michael C. Henry
(74) Attorney, Agent, or Firm—Burns, Doane, Swecker & Mathis, L.L.P.

(57) ABSTRACT

The invention concerns novel troxerutin with high trihydroxy-ethyl-rutin content. Said troxerutin has at least 92 wt. % of 7,3',4'-trihydroxyethyl rutin and a wettability expressed in minutes less than 10 minutes, when said wettability is measured in a test consisting in measuring the time taken by 3.5 g of said enriched troxerutin powder to leave the surface of a beaker containing 100 ml of water, at a stabilised temperature of 20° C., when said enriched troxerutin powder is poured at the surface of the water in said beaker, and a wettability less than 100 seconds when said wettability is measured in a test consisting in measuring the time taken by said enriched troxerutin to be wetted by the water contained in a receptacle, such as a beaker, when said enriched troxerutin has been deposited at the surface of the water, in the form of cores of 2 mm wide and 3 mm high weighing 63 ? 2 mg, at a stabilised temperature of 20° C. Said troxerutin has improved properties of wettability and solubility in water.

19 Claims, No Drawings

TROXERUTIN WITH A HIGH CONTENT OF TRIHYDROXYETHYLRUTOSIDE AND PROCESS FOR ITS PREPARATION

The present invention relates to a preparation with a high content of 7,3',4'-trihydroxyethylrutoside with high wettability, to a pharmaceutical composition based on troxerutin enriched in 7,3',4'-trihydroxyethylrutoside, which has improved solubility, and to a process for preparing them.

7,3',4'-Trihydroxyethylrutoside is the main constituent of troxerutin, which is a composition used therapeutically for treating symptoms in relation with venolymphatic insufficiencies (heavy legs, pain, primo-decubitus restless legs) and the treatment of functional signs associated with an attack of hemorrhoids. Troxerutin consists of a mixture of several derivatives of the flavonoid family, and specifically hydroxyethyl derivatives of rutoside (or rutin). The above-mentioned therapeutic indications are based on the venotonic and vasculoprotective properties of troxerutin. Specifically, the studies performed on animals and man have shown that hydroxyethyl rutosides increase the venous tonus and reduce the capillary permeability.

Patent FR-5072 M describes a troxerutin comprising a mixture of trihydroxyethylrutoside and tetrahydroxyethylrutoside, which has properties of reinforcing the strength of the capillaries, which are useful for treating diseases caused by blood microcirculation disorders. This troxerutin is prepared from rutoside and ethylene carbonate, under hot conditions in the presence of an alkaline catalyst. One variant of this process described in patent FR-A-2 267 327 makes it possible to prepare 7-mono-β-hydroxyethylrutoside, which has comparable activity of regulating capillary permeability and of reinforcing the strength of the capillaries, by reacting ethylene oxide and rutoside in the presence of a complexing agent.

The troxerutin prepared by the usual processes of the art and commonly used nowadays in therapy generally comprises about 80 to 85% of trihydroxyethyl derivative (7,3',4'-trihydroxyethylrutoside), about 8 to 10% of tetrahydroxyethyl derivative (5,7,3',4'-tetrahydroxyethylrutoside) and 4 to 5% of dihydroxyethyl derivative (7,4'-dihydroxyethylrutoside), the remainder consisting of the derivatives 7,3',4'- and 7,5',4'-trihydroxyethylisoquercitrine-3-glucoside and 7,4'-dihydroxyethylkaempferol-3-rutinoside. The troxerutin prepared by the usual techniques is difficult to wet in water, resulting in a long dissolution time, which constitutes a drawback for the preparation of pharmaceutical forms for administration in powder form for solutions, and for the rapid extemporaneous preparation of said solutions by the users for whom these pharmaceutical forms are intended.

The studies undertaken by the Applicant have shown that it is possible to prepare a troxerutin with a high content of 7,3',4'-trihydroxyethylrutoside, and that this preparation (referred to hereinbelow as "enriched troxerutin" on account of its high content of 7,3',4'-trihydroxyethylrutoside) represents the best compromise between the physicochemical properties (wettability in water) and the pharmacodynamic activity (pharmacokinetic constants, including the binding to plasma proteins, and theological properties).

One object of the present invention is thus, more particularly, an enriched troxerutin with a content of at least 92% by weight of 7,3',4'-trihydroxyethylrutoside and a wettability, expressed in minutes, of less than 10 minutes, when this wettability is measured in a test consisting in measuring the time taken for 3.5 g of a powder of this enriched troxerutin to leave the surface of a beaker containing 100 ml of water, at a stabilized temperature of 20° C., when this enriched troxerutin powder is poured onto the surface of the water in this beaker, and having a wettability of less than 100 seconds on average when this wettability is measured in a test consisting in measuring the time taken for this enriched troxerutin to be wetted with the water contained in a container, such as a beaker, when this enriched troxerutin has been placed on the surface of the water, in the form of piles of size 2 and 3 mm in height and weighing 63±2 mg, at a stabilized temperature of 20° C.

Precompacting may be carried out by any suitable type of device for example in a device for producing gel capsules (gel capsule machines).

The invention relates to an enriched troxerutin comprising at least 92% by weight of 7,3',4'-trihydroxyethylrutoside, not more than 5% by weight of 5,7,3',4'-tetrahydroxyethylrutoside, and not more than 4% by weight of 7,4'-dihydroxyethylrutoside, and more particularly an enriched troxerutin of the above type, which contains reduced amounts of 5,7,3',4'-tetrahydroxyethylrutoside (not more than 5% by weight) and of 7,4'-dihydroxyethylrutoside (not more than 4% by weight).

An object of the invention is also a pharmaceutical composition comprising, as active principle, an enriched troxerutin containing at least 92% by weight of 7,3',4'-trihydroxyethylrutoside, this active principle also possibly containing no more than 5% by weight of 5,7,3',4'-tetrahydroxyethylrutoside, and not more than 4% by weight of 7,4'-dihydroxyethylrutoside, these pharmaceutical compositions having advantageous properties which improve their pharmaceutical efficacy, and having good properties of wettability and solubility in water.

In particular, the invention relates to pharmaceutical compositions with high solubility and a high dissolution rate, based on enriched troxerutin combined with an excipient which is suitable for its oral administration—for example an equal weight of mannitol—having a dissolution time of less than 140 seconds on average when this time is measured in a test consisting in pouring 7.25 g of grains into a 250 ml beaker (neck diameter 73 mm, height 95 mm) which contains 200 ml of water (room temperature at about 20° C., stirring with a 35×6.5 mm magnetic bar, machine speed 4 (Ikamag)) and in measuring the dissolution time of the grains.

An object of the present invention is also a novel process for preparing enriched troxerutin with increased wettability, under good yield conditions.

The preparation process in accordance with the present invention consists in reacting rutin under hot conditions with an excess of ethylene oxide in water in the presence of a base, and then n bringing about a crystallization in an alcohol, and it is characterized in that the reaction medium is concentrated so as to obtain, in the crystallization medium, a water content of less than 8%, and preferably between 1% and 6%.

According to one preferential embodiment of the process of the invention, the crystallization is carried out in an alcohol selected from methanol and isopropanol, separately or, preferably, as a mixture, at a crystallization end temperature of between 35° C. and 15° C. It is most particularly advantageous to carry out the crystallization by selecting a temperature descent profile which is adapted to the crystallization kinetics of the trihydroxyethyl derivative relative to the di- and tetrahydroxyethyl derivatives of rutoside. Specifically, the operating conditions according to the process of the invention, by applying a rapid temperature descent and predefined solvent ratios, make it possible to bring about the preferential precipitation of the trihydroxyethyl derivative and to limit the precipitation of the tetra- and dihydroxyethyl derivatives, the final concentration in the medium being insufficient to allow the latter derivatives to crystallize.

As mentioned above, the speed of temperature descent must be fast, under industrial use conditions, and preferably greater than about 20° C. per hour and preferably 30° C. per hour.

The base added to the reaction medium may be chosen from sodium or potassium hydroxide, or sodium, potassium, lithium or calcium carbonate.

An enriched troxerutin comprising at least 92% by weight of 7,3',4'-trihydroxyethylrutoside, not more than 5% by weight of 5,7,3',4'-tetrahydroxyethylrutoside and not more than 4% by weight of 7,4'-dihydroxyethylrutoside is thus obtained. Preferably, the content of 7,4'-dihydroxyethylrutoside is between 1% and 3% by weight, while the content of 5,7,3',4'-tetrahydroxyethylrutoside is between 2% and 4% by weight.

Advantageously, the enriched troxerutin of the invention comprises at least 93% of 7,3',4'-trihydroxyethylrutoside, 2% to 3.5% of 5,7,3',4'-tetrahydroxyethylrutoside and 1.7% to 2.5% of 7,4'-dihydroxyethylrutoside. As mentioned above, it may contain a few traces of derivatives 7,3',4'- and 7,5',4'-trihydroxyethylisoquercitrine-3-glucoside and 7,4'-dihydroxy-ethylkaempferol-3-rutinoside.

The enriched troxerutin in accordance with the present invention contains at least 92% by weight of 7,3',4'-trihydroxyethylrutoside, as mentioned above. It may also contain the isomer consisting of 5,7,4'-trihydroxyethylrutoside, which cannot be readily distinguished from the above isomer by common analytical techniques. In the present description, the name 7,3',4'-trihydroxyethylrutoside should also, if need be, encompass the second isomer. Similarly, the name 7,4'-dihydroxyethylrutoside may, where appropriate, encompass the isomer 7,3'-dihydroxyethylrutoside.

The enriched troxerutin prepared according to the invention and having the con tents indicated above of di-, tri- and tetrahydroxyethyl rutoside derivatives, has advantageous properties. In particular, the enriched troxerutin of the invention has good wettability in water and improved inhibition of red blood cell aggregation wren compared with the usual troxerutins.

Specifically, the ex vivo studies performed on human blood have shown that the inhibition of red blood cell aggregation was significantly improved in the presence of tri- or tetrahydroxyethylrutosides and that the trihydroxyethyl derivative is more effective than the tetrahydroxyethyl derivative. This difference in efficacy was confirmed by the superiority of the enriched troxerutin according to the invention (trihydroxyethylrutoside content in the region of 95%) compared with commercially available troxerutins (content in the region of 84%). The advantage of decreasing the aggregation of red blood cells lies in a reduction in the total blood viscosity, and consequently in better fluidity of the blood. This property is manifested by an increase in the venous return and in the microcirculatory flow rate (increase in the density of the infused capillaries).

The wettability of the enriched troxerutin prepared according to the invention was compared with that of commercially available troxeretins comprising about 84% of trihydroxyethyl derivative, about 8% of tetrahydroxyethyl derivative and about 4% of dihydroxyethyl derivative of rutoside, the remainder consisting of the abovementioned hydroxyethyl derivatives of isocuercitrine-3-glucoside and of kaempferol-3-rutinoside.

3.5 g of enriched troxerutin to be tested are poured into a 250 ml beaker (low shape) containing 100 ml of water, the temperature of which is stabilized to that of the laboratory (at about 20° C.). The temperature at the start of the test is recorded and the time required for the enriched troxerutin to be totally wet, that is to say for it all to fall to the bottom of the beaker, is measured.

The table below indicates the time required to achieve a dispersion close to 100%, measured on three samples of an enriched troxerutin of the invention and commercial troxerutins. Each test was carried out by maintaining the temperature of the aqueous solution at 20° C., without stirring.

Comparative table

| Troxerutin | Time (min) | Average (min.) | Standard deviation |
|---|---|---|---|
| Invention | 3.5 | 5.5 | 2.6 |
|  | 4.5 |  |  |
|  | 8.4 |  |  |
| Comparison | 65 | 69.3 | 4.0 |
|  | 70 |  |  |
|  | 73 |  |  |

Similarly, enriched troxerutin is deposited in the form of a pile of powder of size 2 and 3 mm in height and weighing 63±3 mg on the surface of an 800 ml beaker containing 100 ml of water. The temperature of the water at the start of the test is recorded and the time required for the enriched troxerutin to be totally wet, that is to say for it all to change color, is measured.

The table below indicates the average time required to wet piles of enriched troxerutin of the invention and commercial troxerutin.

| Troxerutin | Average time (sec) |
|---|---|
| Invention | <100 sec |
| Comparison | 325 sec |

The results of the above two tests show that the enriched troxerutin of the invention differs from the reference troxuretins by a markedly improved wettability.

The study performed on pharmaceutical compositions based on enriched troxeritin in accordance with the present invention showed that the rheological properties demonstrated depend essentially on high doses of 7,3',4'-trihydroxyethylrutoside, that is to say at least 92%; specifically in vitro studies have established a relationship between the phenomena of rheological correction (improvement in the aggregation kinetics and the deaggregation constants for red blood cells) and the concentration of 7,3',4'-trihydroxyethylrutoside.

Furthermore, it has been found that the enriched troxerutin of the invention is less bound to plasma proteins, which limits the risk of drug interaction. This advantage is all the more important in the case of elderly patients who may need to take several medicaments.

The pharmaceutical compositions based on enriched troxerutin show better solubilization, in particular under the following conditions.

A mixture is prepared containing, for example: 500 g of the enriched troxerutin to be tested, 500 g of mannitol and 0.035 g of sodium saccharinate. The compounds are mixed together and granulated with an ethanol/water mixture.

The grains obtained are oven-dried. The dry grains are calibrated on a screen with a nominal mesh diameter of 800 μm, and 35.71 g of orange flavoring are then added thereto. Mixing is carried cut to homogenize, for 5 min. 7.25 g of grains are poured into a 250 ml beaker (neck diameter 78 mm, height 95 mm) which contains 200 ml of water room temperature at about 20° C., stirring with a 35±6.5 mm magnetic bar, machine speed 4 (Ikamag)). The time required for the grains to dissolve is measured.

RESULTS

|  | Average in seconds |
| --- | --- |
| Pharmaceutical composition based on enriched troxerutin | <140 |
| Pharmaceutical composition based on conventional troxerutin | 226 |

A large increase in the solubilization of the finished product manufactured with the enriched troxerutin of the invention is observed. The final pharmaceutical compositions based on enriched troxerutin also require smaller volumes of wetting liquid to carry out the operations required for the granulation, when the product must finally be presented in the form of granules. From 150 g of water to wet 1000 g of a preparation based on conventional troxerutin and a similar weight of mannitol, less than 100 g of water is now required to wet the same amount of composition according to the invention based on purified troxerutin.

RESULTS

|  | Wetting liquid in g |
| --- | --- |
| Pharmaceutical composition based on enriched troxerutin | <100 g |
| Pharmaceutical composition based on conventional troxerutin | 150 g |

The examples which follow illustrate the invention in greater detail without limiting its scope. Except where otherwise mentioned, al the parts and percentages are expressed on a weight basis.

EXAMPLE 1

100 g rutin are treated under hot conditions, at about 75° C., with 28 g of ethylene oxide in 100 ml of water containing 1.1 g of sodium hydroxide, and the reaction mixture is kept stirring for about 6 hours. The reaction is monitored by HPLC chromatography, and the end of the reaction is detected when the relative proportions of di-, tri- and tetrahydroxyethyl rutoside derivatives are, respectively, 4%, 88% and 7 to 8%. The medium is then acidified by adding sulfuric acid to neutralize the alkali which is present.

The aqueous medium is concentrated under reduced pressure (about $2 \times 10^4$ Pa) at a temperature of between 60 and 70° C., such that the water concentration is close to 2% in the final crystallization medium.

The concentrate is taken up in 240 ml of methanol and is then filtered to remove the salts formed. 220 ml of isopropanol are added to the solution and, after checking the water content, crystallization is carried out over about 8 hours, the temperature being decreased from 65° C. to 25° C. over the first two hours and being maintained between 25 and 20° C. during the next 6 hours.

89.4 g (80% yield) of troxerutin with a titer of 92% of trisubstituted derivative, 4% of tetrasubstituted derivative and 3% of disubstituted derivative are thus obtained, the remainder consisting of the abovementioned hydroxyethyl derivatives of isoquercitrine-3-glucoside and of kaempferol-3-rutinoside.

EXAMPLE 2

The process is performed as in example 1, but the crystallization is carried out over about 3 to 4 hours, during which the temperature is decreased from 65° C. to 30° C. and is then maintained at between 30 and 25° C. over about 2 hours.

87.2 g (78% yield) of troxerutin with a titer of 93% of trisubstituted derivative, 3.5% of tetrasubstituted derivative and 2.5% of disubstituted derivative are thus obtained, the remainder consisting of the same derivatives as above.

EXAMPLE 3

The process is performed as in example 1, but the aqueous solution is passed over ion-exchange resins or strong cationic type, and then of strong anionic type, before filtration. The medium is then concentrated so as to bring the water content to a value equal to about 5.2% in the final medium.

The concentrate is taken up in 800 ml of methanol and 30 ml of isopropanol solution are added. The crystallization is carried out as above, over about 2 hours, while maintaining the temperature at between 25 and 15° C. over about 1 hour at the end of crystallization.

84.2 g (75% yield) of troxerutin with a titer of 95% of trisubstituted derivative, 2.8% of tetrasubstituted derivative and 1.7% of disubstituted derivative are thus obtained, the remainder consisting of the same derivatives as above.

What is claimed is:

1. An enriched troxerutin, characterized in that it comprises at least 92% by weight of 7,3',4'-trihydroxyethylrutoside, from 2% to 4% by weight of tetrahydroxyethyl rutoside and between 1% and 3% by weight of 7,4'-dihydroxyethylrutoside.

2. The enriched troxerutin of claim 1,
wherein the troxerutin has a wettability, expressed in minutes, of less than 10 minutes when this wettability is measured in a test consisting of measuring the time taken for 3.5 g of a powder of the enriched troxerutin to leave the surface of a beaker containing 100 mL of water, at a stabilized temperature of 20° C., when this enriched troxerutin powder is poured onto the surface of the water in this beaker, and
wherein the troxerutin has a wettability of less than 100 seconds on average when the wettability is measured in a test consisting of measuring the time taken for this enriched troxerutin to be wetted with the water contained in a container when the enriched troxerutin has been placed on the surface of the water, in the form of piles of size 2 and 3 mm in height and weighing 63±2 mg, at a stabilized temperature of 20° C.

3. The enriched troxerutin as claimed in claim 1, characterized in that its content of 7,3',4'-trihydroxyethylrutoside is greater than or equal to 93% by weight.

4. The enriched troxerutin as claimed in claim 1, characterized in that it comprises at least 93% of 7,3',4'- trihydroxyethylrutoside, 2% to 3.5% of 5,7,3',4'-tetrahydroxyethylrutoside and from 1.7% to 2.5% of 7,4'-dihydroxyethylrutoside.

5. The enriched troxerutin as claimed in claim 2, in combination with a pharmaceutical excipient.

6. A pharmaceutical composition with high solubility and a high dissolution speed, based on enriched troxerutin combined with an excipient which is suitable for its oral administration having a dissolution time of less than 140 seconds on average when this time is measured in a test consisting in pouring 7.25 g of grains into a 250 ml beaker (neck diameter 78 mm, height 95 mm) which contains 200 ml of water (room temperature at about 20° C., stirring with a 35×6.5 mm magnetic bar, machine speed 4 (Ikamag)) and in measuring the dissolution time of the grains.

7. The composition as claimed in claim 6, characterized in that the active principle, of which 7,3',4'-trihydroxyethylrutoside forms a part, consists of an enriched troxerutin in which the 7,3'4'-trihydroxyethylrutoside is in an amount of at least 92% by weight.

8. The composition as claimed in claim 7, characterized in that the enriched troxerutin comprises at least 92% by weight of 7,3',4'-trihydroxyethylrutoside, not more than 5% by weight of 5,7,3',4'-tetrahydroxyethylrutoside and not more than 4% by weight of 7,4'-dihydroxyethylrutoside.

9. A process for preparing troxerutin comprising at least 92% by weight of 7,3',4'-trihydroxyethylrutoside, from 2% to 4% by weight of tetrahydroxyethyl rutoside of 5,7,3',4'-tetrahydroxyethylrutoside and between 1% and 3% by weight 4% of 7,4'-dihydroxyethylrutoside, which consists in reacting rutin, under hot conditions, with an excess of ethylene oxide in water in the presence of a base, and then in bringing about a crystallization in an alcohol, characterized in that the reaction medium is concentrated so as to obtain, in the crystallization medium, a water content comprising between 1% and 8%.

10. The process as claimed in claim 9 characterized in that the water content is between 1% and 6%.

11. The process as claimed in claim 10, characterized in that the crystallization solvent is methanol or isopropanol, alone or as a mixture.

12. The process as claimed in claim 11, characterized in that the crystallization is carried out with a temperature descent speed of greater than 20° C. per hour over 1 to 2 hours.

13. The process as claimed in claim 12, characterized in that the crystallization is carried out at a temperature of between 35° C. and 15° C.

14. The composition as claimed in claim 7, characterized in that the enriched troxerutin comprises at least 93% by weight of 7,3',4'-trihydroxyethylrutoside is greater than or equal to 93% by weight.

15. The composition as claimed in claim 7, characterized in that the enriched troxerutin comprises at least 92% by weight of 7,3',4'-trihydroxyethyrutoside, not more than 5% by weight of 5,7,3',4'-tetrahydroxyethylrutoside and between 1% and 3% by weight of 7,4'-dihydroxyethylrutoside.

16. The composition as claimed in claim 7, characterized in that the enriched troxerutin comprises at least 92% by weight of 7,3',4'-trihydroxyethylrutoside, between 2% and 4% by weight of 5,7,3',4'-tetrahydroxyethylrutoside and not more than 4% by weight of 7,4'-dihydroxyethylrutoside.

17. The composition as claimed in claim 7, characterized in that the enriched troxerutin comprises at least 93% of 7,3',4'-trihydroxyethylrutoside, 2% to 3.5% of 5,7,3',4'-tetrahydroxyethylrutoside and from 1.7% to 2.5% of 7,4'-dihydroxyethylrutoside.

18. The enriched troxerutin of claim 2, wherein the container is a beaker.

19. A pharmaceutical composition as claimed in claim 5 where the pharmaceutical excipient is suitable for oral administration.

* * * * *